US009474550B2

(12) United States Patent
Jakubow

(10) Patent No.: US 9,474,550 B2
(45) Date of Patent: Oct. 25, 2016

(54) EXFOLIATION UNIT WITH VACUUM MEANS

(71) Applicant: Rafael Jakubow, Golden Beach, FL (US)

(72) Inventor: Rafael Jakubow, Golden Beach, FL (US)

( * ) Notice: Subject to any disclaimer, the term of this patent is extended or adjusted under 35 U.S.C. 154(b) by 322 days.

(21) Appl. No.: 14/194,631

(22) Filed: Feb. 28, 2014

(65) Prior Publication Data

US 2015/0245853 A1   Sep. 3, 2015

(51) Int. Cl.
*A61B 17/54* (2006.01)
*A61B 17/32* (2006.01)
*A61B 17/00* (2006.01)

(52) U.S. Cl.
CPC ...... *A61B 17/54* (2013.01); *A61B 2017/00734* (2013.01); *A61B 2017/00761* (2013.01); *A61B 2017/320004* (2013.01); *A61B 2218/007* (2013.01)

(58) Field of Classification Search
CPC ............ A61B 2017/00761; A61B 17/320004; A61B 17/00747; A61B 2218/007; A61B 17/54
See application file for complete search history.

(56) References Cited

U.S. PATENT DOCUMENTS

| 2004/0092895 A1* | 5/2004 | Harmon | A61B 17/54 604/289 |
| 2010/0198119 A1* | 8/2010 | Gubernick | A45D 34/04 601/69 |
| 2011/0082415 A1* | 4/2011 | Ignon | A61B 17/54 604/22 |
| 2013/0138119 A1* | 5/2013 | Luzon | A61B 17/54 606/131 |
| 2013/0158547 A1* | 6/2013 | David | A61B 18/14 606/41 |

\* cited by examiner

*Primary Examiner* — Julie A Szpira
(74) *Attorney, Agent, or Firm* — Frank L. Kubler

(57) ABSTRACT

An exfoliation includes a unit handle which is hollow and has a handle proximal end and a handle distal end, and has an air receiving port in the handle distal end and an air discharge port in the handle proximal end; an abrasion rim adjacent to the air receiving port having an abrasive surface; an air passageway in fluid communication with the air receiving port and the air discharge port; and with vacuum mechanism in fluid communication with the air passageway for drawing an air stream into the air receiving port, passing the air stream through the air passageway and discharging the air stream from the air discharge port. The unit preferably additionally includes a debris gathering chamber in fluid communication with the air passageway for collecting and retaining debris particles in the air stream.

8 Claims, 3 Drawing Sheets

EXFOLIATION UNIT WITH VACUUM MEANS

BACKGROUND OF THE INVENTION

1. Field of the Invention

The present invention relates generally to the field of cosmetics application devices including brushes. More specifically the present invention relates to an exfoliation unit including a unit handle which is hollow and preferably elongate and tubular to be easily gripped by a user and with a handle proximal end and a handle distal end, and an air receiving port in the handle distal end and an air discharge port in the handle proximal end. The air receiving port is encircled by an outwardly protruding annular abrasion rim having a rough surface similar to that of sandpaper and which is in fluid communication with a debris gathering chamber and with vacuum means drawing air into the air receiving port and discharging the air from the air discharge port.

The handle distal end preferably is externally convex to define a dome within the hollow unit handle and the debris gathering chamber is in turn defined by the interior of the dome and a cross-sectional dividing wall across the base of the dome within the unit housing, but may take the form of any suitable chamber within the unit handle or otherwise connected to the unit. An air passing port is provided in the dividing wall adjacent to a lateral edge of the dividing wall and a barrier wall protrudes distally from the dividing wall immediately adjacent to the air passing port toward but leaving a gap between the distal region of the dome and the dividing wall. As a result, the air stream enters the debris gathering chamber through the air receiving port one a first side of the dividing wall and follows a path which initially is directed proximally, then doubles back to flow distally and to enter and pass through the gap and then to flow along the second side of the dividing wall and through the air passing port to continue through the passageway, through the blower and out of the unit through the air discharge port. The dividing wall preferably is tubular and has an open distal end. As the air stream doubles back within the debris gathering chamber, most particles such as exfoliated skin cells contained within the air stream drop into and remain within the debris gathering chamber. To remove gathered particles from the debris gathering chamber, the blower motor is deactivated and the unit can be inverted so that the particles simply drop out of the unit through the air receiving port and into any selected waste receptacle.

The vacuum means preferably includes an air passageway in the form of an air passing conduit extending from the air receiving port through the hollow handle, alternatively in the form of the entire interior of the hollow handle, and opening out of an air discharge port in the handle proximal end. The unit handle additionally contains a blower in fluid communication with the air passageway for blowing a stream of air through the passageway from the air entry port through the passageway and out of the air discharge port, and an electric motor in drivable relation to and operating the blower, and an electric motor circuit including an activation switch mounted in the handle wall to be accessible to user fingers outside the handle, the motor circuit being connected to a power source. Preferred power sources include an electric cord extending through a cord port outside the unit handle with an external plug for fitting into a conventional wall outlet, and household batteries such as a pair of C or D batteries contained within a battery compartment within the unit handle having a battery access door opening out of the handle wall. The blower and blower motor preferably are supported and held in place within the unit housing by handle internal mounting structures configured as needed.

To use the unit, the user simply operates the activation switch to activate the blower motor and gently rubs abrasion rim against his or her skin. The abrasion produced by rubbing contact with the abrasion rim exfoliates the skin and exfoliated skin cells or other dislodged debris is immediately drawn into the debris gathering chamber by the vacuum action of the air stream produced by the blower. Then, as noted above, when the user has finished, the user uses the activation switch to shut off the blower motor and periodically empties gathered debris from the chamber.

2. Description of the Prior Art

There have long been exfoliation devices for abrading dead skin cells from the surface of user skin. A problem with these devices has been that there has been no entirely effective means for gathering skin cells exfoliated by these devices.

It is thus an object of the present invention to provide an exfoliation unit which immediately and reliably gathers dislodged skin cells as soon as they are exfoliated from the user skin.

It is another object of the present invention to provide such a unit which is easy to hold, operate and clean.

It is finally an object of the present invention to provide such a unit which is highly inexpensive to manufacture.

SUMMARY OF THE INVENTION

The present invention accomplishes the above-stated objectives, as well as others, as may be determined by a fair reading and interpretation of the entire specification.

An exfoliation unit preferably includes a unit handle which is hollow and has a handle proximal end and a handle distal end, and has an air receiving port in the handle distal end and an air discharge port in the handle proximal end; an abrasion rim adjacent to the air receiving port having an abrasive surface; an air passageway in fluid communication with the air receiving port and the air discharge port; and with vacuum mechanism in fluid communication with the air passageway for drawing an air stream into the air receiving port, passing the air stream through the air passageway and discharging the air stream from the air discharge port.

The unit handle preferably is elongate and tubular to be easily gripped by a user. The abrasion rim preferably is annular and encircles the air receiving port.

The unit preferably additionally includes a debris gathering chamber in fluid communication with the air passageway for collecting and retaining debris particles in the air stream. The debris gathering chamber preferably includes a hollow dome within the hollow unit handle having a dome base; a cross-sectional dividing wall having a lateral edge extending across the dome base having an air passing port adjacent to the lateral edge of the dividing wall; and a barrier wall protruding distally from the dividing wall adjacent to the air passing port extending toward but leaving a gap between the dome and the barrier wall, so that the air stream enters the debris gathering chamber through the air receiving port on a first side of the barrier wall and follows a path which initially is directed proximally, then doubles back to flow distally and to enter and pass through the gap and then to flow along the second side of the barrier wall and through the air passing port to continue through the passageway, through the blower and out of the unit through the air discharge port.

The vacuum means preferably includes a blower in fluid communication with the air passageway for blowing a stream of air through the passageway from the air entry port through the passageway and out of the air discharge port, and an electric motor in drivable relation to and operating the blower, and an electric motor circuit including an activation switch mounted in the handle wall to be accessible to user fingers outside the handle, the motor circuit being connectable to a power source. The power source preferably is a battery.

BRIEF DESCRIPTION OF THE DRAWINGS

Various other objects, advantages, and features of the invention will become apparent to those skilled in the art from the following discussion taken in conjunction with the following drawings, in which.

DETAILED DESCRIPTION OF THE PREFERRED EMBODIMENTS

Figure 1:
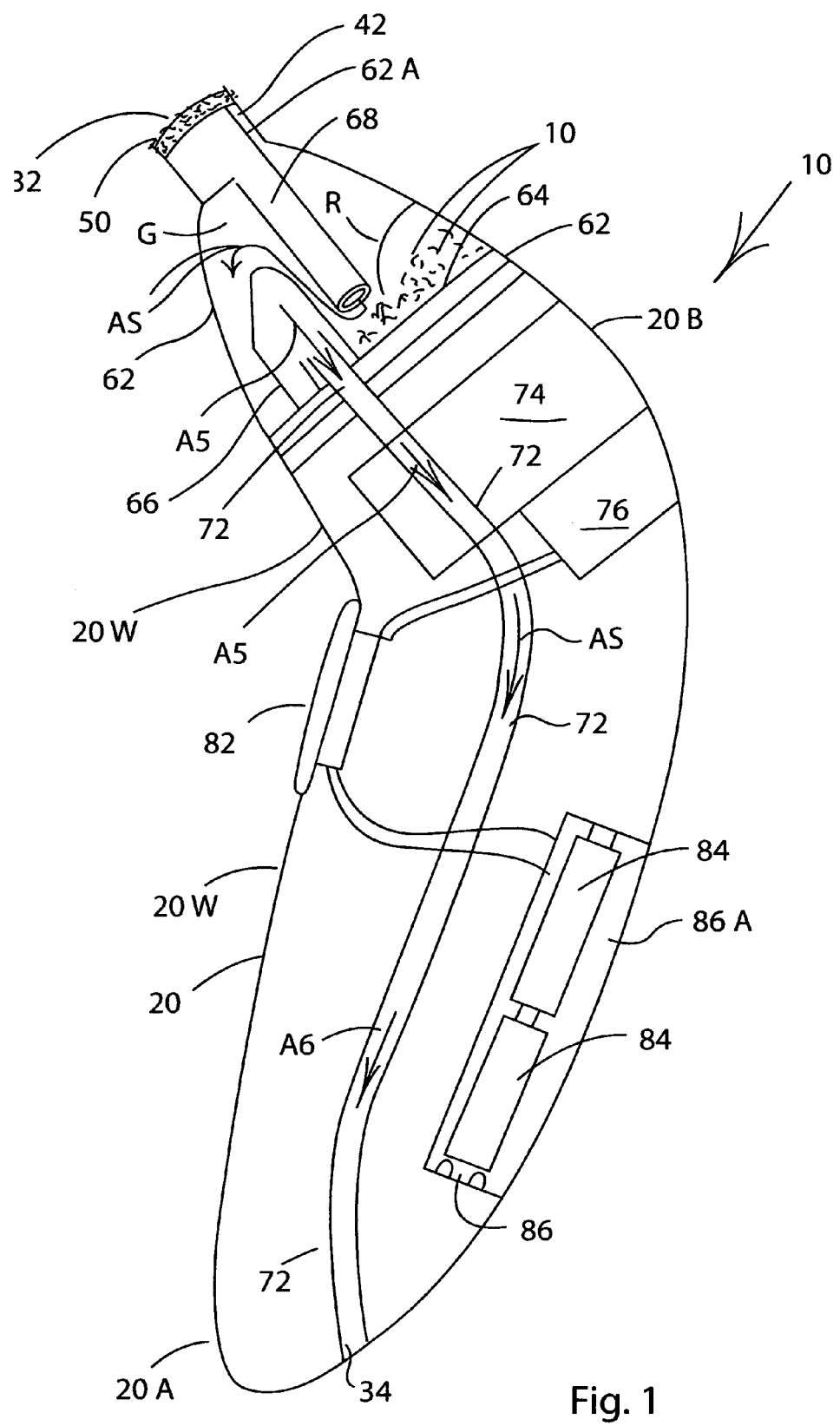
FIG. 1 is a cross-sectional side view of the preferred exfoliation unit.

As required, detailed embodiments of the present invention are disclosed herein; however, it is to be understood that the disclosed embodiments are merely exemplary of the invention which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Reference is now made to the drawings, wherein like characteristics and features of the present invention shown in the various FIGURES are designated by the same reference numerals.

First Preferred Embodiment

Figure 2:
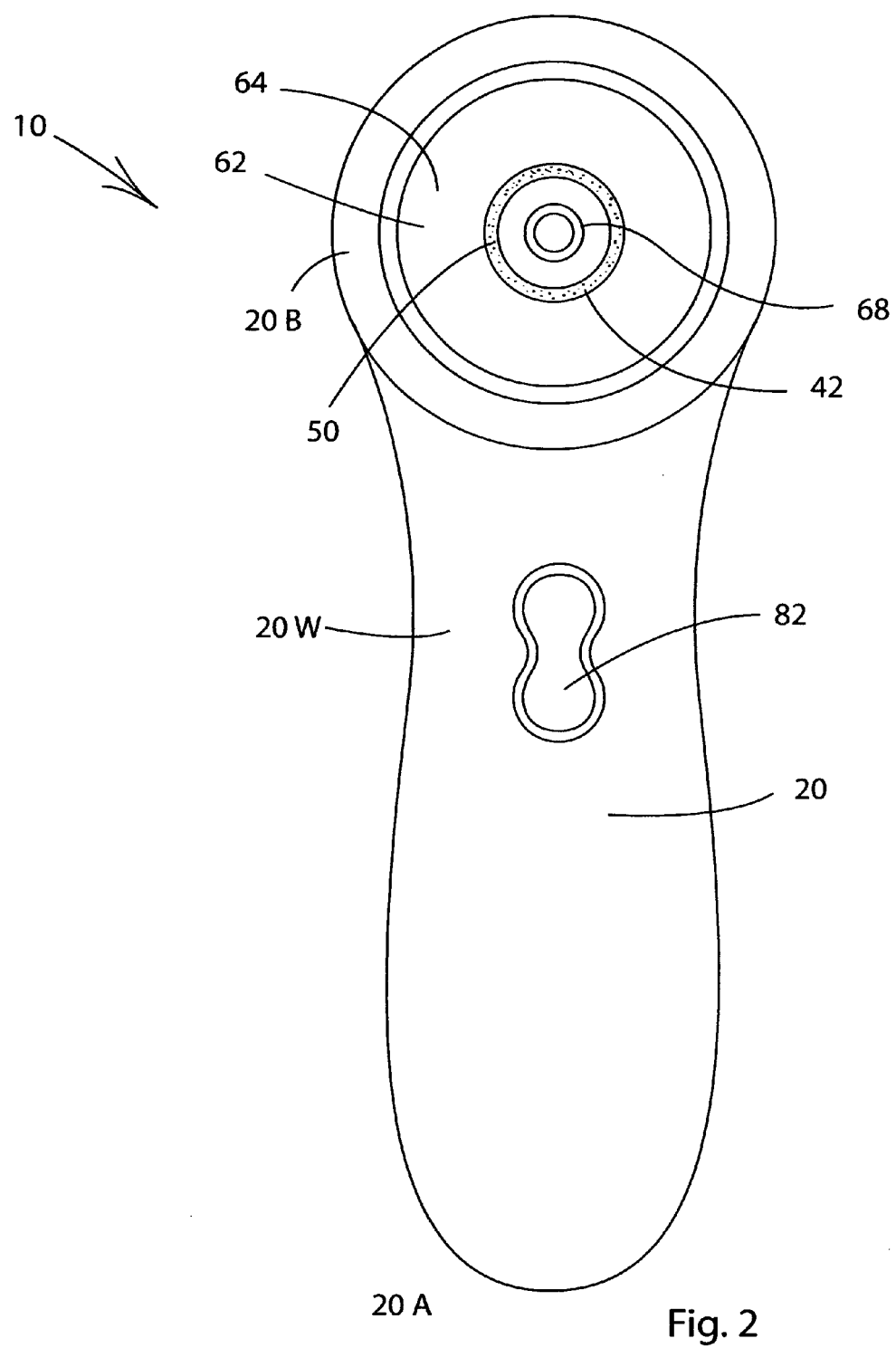
FIG. 2 is a front view of the unit of FIG. 1.
Figure 3:
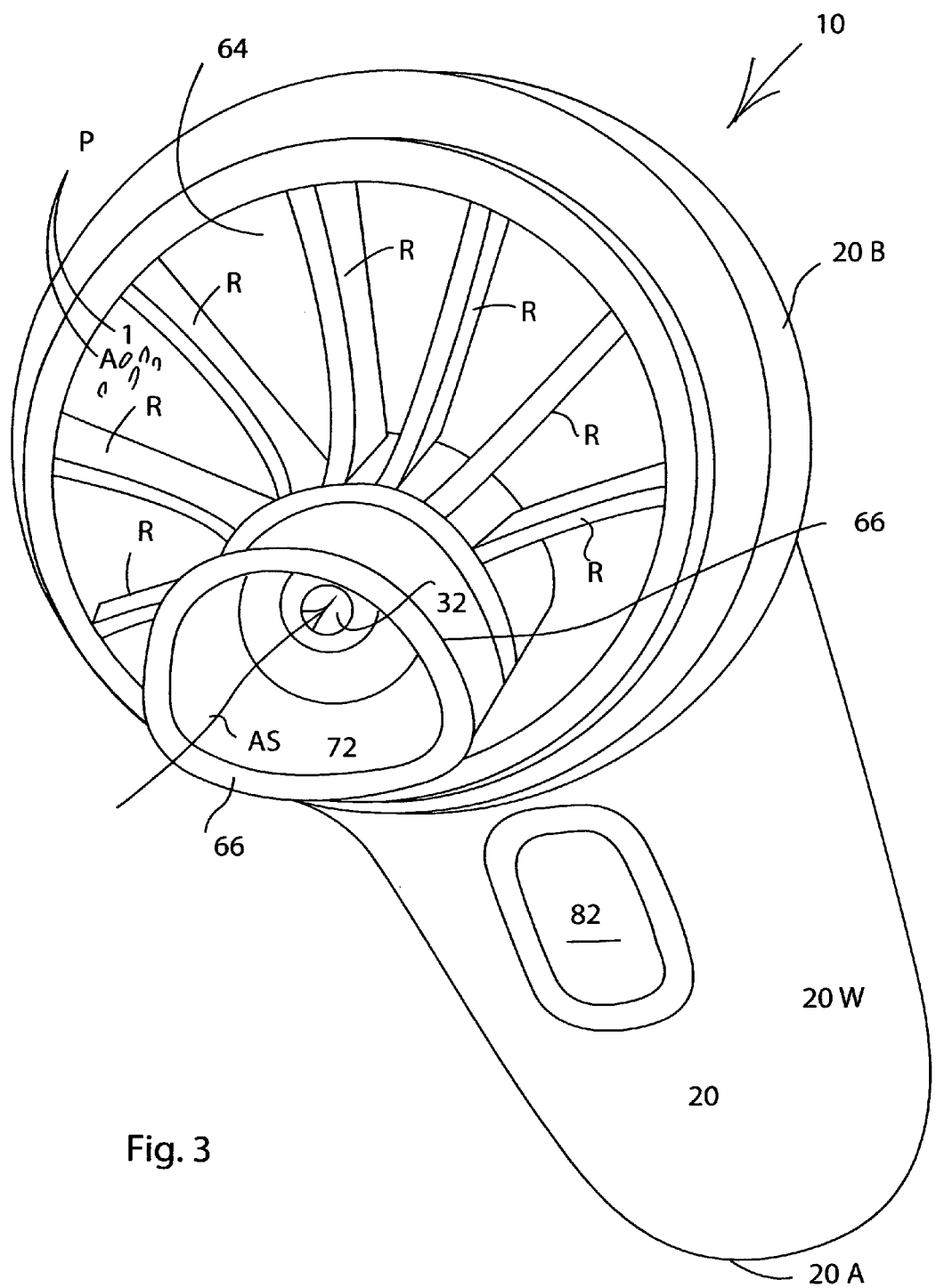
FIG. 3 is a close-up perspective view of the unit distal end with the dome removed.

Referring to FIGS. 1-3, an exfoliation unit 10 is disclosed including a unit handle 20 which is hollow and preferably tubular with a handle proximal end 20A and a handle distal end 20B, the unit handle 20 having an air receiving port 32 in the handle distal end 20B and an air discharge port 34 in the handle proximal end 20A. The air receiving port 32 is encircled by an outwardly protruding annular abrasion rim 50 having a rough surface similar to that of sandpaper which is in fluid communication with a debris gathering chamber 60 and with vacuum means 70 drawing air into the air receiving port 32 and discharging the air from the air discharge port 34.

The handle distal end 20B preferably is externally convex to define a dome 62 within the hollow unit handle 20 and the debris gathering chamber 60 is in turn defined by the interior of the dome 62 and a cross-sectional dividing wall 64 across the base of the dome 62 within the unit housing 20, but may take the form of any suitable chamber within the unit handle 20 or otherwise connected to the unit 10. An air passing port 36 is provided in the dividing wall 64 adjacent to a circumferential edge 64A of the dividing wall 64 and a barrier wall 66 protrudes distally from the dividing wall 64 immediately adjacent to an air passing port 36, leaving a gap G between the distal region of the dome 62 and the dividing wall 64. As a result, the air stream AS enters the debris gathering chamber 60 through the air receiving port 32 on a first side of the dividing wall 64 and follows a path P which initially is directed proximally, then doubles back to flow distally and to enter and pass through the gap G and then to flow through a guide tube 68 projecting inwardly from the dome 62 and then into and through the distal open end of the preferably tubular barrier wall 66 and through the air passing port 36 to continue through the passageway 72, through the blower 74 and out of the unit 10 through the air discharge port 34. Passageway 72 preferably protrudes distally within a segment of the tubular barrier wall 66. As the air stream AS doubles back within the debris gathering chamber 60, most particles P such as of exfoliated skin cells contained within the air stream AS drop out of the air stream into and remain within the debris gathering chamber 60. Distally protruding ribs R preferably are provided on the dividing wall 64 distal face to form compartments to help trap and retain particles P. To remove gathered particles P from the debris gathering chamber 60, the blower motor 74 is deactivated and the unit 10 can be inverted so that the particles P simply drop out of the unit 10 through the air receiving port 32 and into any selected waste receptacle. The abrasion rim 50 preferably is provided on the distal end of a rim tube 42 removably and snugly fitted over a tubular dome opening flange 62A encircling and partially defining the air receiving port 32 integral with and protruding distally from the dome 62.

The vacuum means 70 preferably includes air passageway 72 in the form of an air passing conduit extending from the air receiving port 32 through the interior of the hollow unit handle 20, the air passageway 72 alternatively taking the form of the entire interior of the hollow handle 20, and opening out of the air discharge port 34 in the handle proximal end 20A. The unit handle 20 additionally contains blower 74 in fluid communication with the air passageway 72 for blowing a stream of air AS through the passageway 72 from the air entry port 32 through the passageway 72 and out of the air discharge port 34, and an electric motor 76 connected in drivable relation to and operating the blower 74, and an electric blower motor circuit 78 including an on-off or activation switch 82 mounted in the handle wall 20W to be accessible to user fingers outside the handle 20, the motor circuit 78 being connected to a power source 84. Preferred power sources 84 include an electric cord (not shown) extending through a cord port outside the unit handle 20 with an external plug for fitting into a conventional wall outlet, and household batteries BAT such as a pair of C or D batteries contained within a battery compartment 86 within the unit handle 20 having a battery access door 86A opening out of the handle wall 20W. The blower 74 and blower motor 76 preferably are supported and held in place within the unit housing 20 by handle internal mounting structures MS configured as needed.

To use the unit 10, the user simply operates the activation switch 82 to activate the blower motor 76 and gently rubs abrasion rim 50 against his or her skin. The abrasion produced by rubbing contact with the abrasion rim 50 exfoliates the skin and exfoliated skin cells or other dislodged debris P is immediately drawn into the debris gathering chamber 60 by the vacuum action of the air stream AS produced by the blower 74. Then, as noted above, when the user has finished, the user operates the activation switch 82 to shut off the blower motor 76, and periodically empties gathered debris P from the chamber 60.

While the invention has been described, disclosed, illustrated and shown in various terms or certain embodiments or modifications which it has assumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

I claim as my invention:

1. An exfoliation unit, comprising:
a unit handle which is hollow and has a handle proximal end and a handle distal end, and has an air receiving port in said handle distal end and an air discharge port in said handle proximal end;
an abrasion rim adjacent to said air receiving port having an abrasive surface;
an air passageway in fluid communication with said air receiving port and said air discharge port;
vacuum means comprising a blower in fluid communication with said air passageway for drawing an air stream into, and thereby creating a vacuum at the air receiving port and for blowing the stream of air through said passageway and out of said air discharge port;
and a debris gathering chamber in fluid communication with said air passageway for collecting and retaining debris particles in said air stream, said debris gathering chamber comprising a hollow dome within said hollow unit handle having a dome base; a cross-sectional dividing wall having a lateral edge extending across said dome base having an air passing port adjacent to said lateral edge of said dividing wall; and a barrier wall protruding distally from said dividing wall adjacent to said air passing port extending toward but leaving a gap between said dome and said barrier wall; such that the air stream enters the debris gathering chamber through the air receiving port on a first side of the barrier wall and follows a path which initially is directed proximally, then doubles back to flow distally and to enter and pass through the gap and then to flow proximally along the second side of the barrier wall and through the air passing port to continue through the passageway, through the blower and out of the unit through the air discharge port.

2. The unit of claim 1, wherein said unit handle is elongate and tubular to be easily gripped by a user.

3. The unit of claim 1, wherein said abrasion rim is annular and encircles said air receiving port.

4. The unit of claim 1, additionally comprising an electric motor in drivable relation to and operating said blower, and an electric motor circuit including an activation switch mounted in said handle wall to be accessible to user fingers outside said handle, said motor circuit being connectable to a power source.

5. The unit of claim 4, wherein said power source is a battery.

6. The unit of claim 1, additionally comprising distally protruding ribs on said dividing wall distal face for forming compartments for trapping and releasibly retaining a quantity of the debris particles.

7. The unit of claim 1, additionally comprising distally protruding ribs on said dividing wall distal face for forming compartments for trapping and retaining a quantity of the debris particles.

8. An exfoliation unit, comprising:
a unit handle which is hollow and has a handle proximal end and a handle distal end, and has an air receiving port in said handle distal end and an air discharge port in said handle proximal end;
an abrasion rim adjacent to said air receiving port having an abrasive surface;
an air passageway in fluid communication with said air receiving port and said air discharge port;
vacuum means comprising a blower in fluid communication with said air passageway for drawing an air stream into, and thereby creating a vacuum at the air receiving port and for blowing the stream of air through said passageway and out of said air discharge port;
and a debris gathering chamber in fluid communication with said air passageway for collecting and retaining debris particles in said air stream, said debris gathering chamber being contained within said hollow unit handle and comprising a cross-sectional dividing wall extending across and within said hollow unit handle and having an air passing port adjacent to said lateral edge of said dividing wall, and a barrier wall protruding distally from said dividing wall adjacent to said air passing port; such that the air stream enters the debris gathering chamber through said air receiving port on a first side of said barrier wall and follows a path which initially is directed proximally, then doubles back to flow distally and to enter and pass over said barrier wall and then to flow proximally along the second side of the barrier wall and through the air passing port to continue through the passageway, through the blower and out of the unit through the air discharge port.

* * * * *